United States Patent
Linder et al.

(10) Patent No.: US 8,121,678 B2
(45) Date of Patent: Feb. 21, 2012

(54) IMPLANTABLE MEDICAL DEVICE WITH HALL SENSOR

(75) Inventors: William J. Linder, Golden Valley, MN (US); Angela M. Muttonen, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 527 days.

(21) Appl. No.: 12/330,349

(22) Filed: Dec. 8, 2008

(65) Prior Publication Data

US 2009/0157146 A1 Jun. 18, 2009

Related U.S. Application Data

(60) Provisional application No. 61/007,455, filed on Dec. 12, 2007.

(51) Int. Cl.
*A61N 1/36* (2006.01)

(52) U.S. Cl. ............................................... 607/2; 607/63

(58) Field of Classification Search .................... 607/63, 607/65, 2, 18, 59, 36, 62, 64, 67, 75
See application file for complete search history.

(56) References Cited

U.S. PATENT DOCUMENTS

| | | | |
|---|---|---|---|
| 3,311,111 A | 3/1967 | Bowers | |
| 4,301,804 A * | 11/1981 | Thompson et al. | ............. 607/30 |
| 4,721,114 A | 1/1988 | DuFault et al. | |
| 4,793,361 A | 12/1988 | DuFault | |
| 4,799,486 A | 1/1989 | DuFault | |
| 4,799,493 A | 1/1989 | DuFault | |
| 5,634,938 A | 6/1997 | Swanson et al. | |
| 5,662,694 A | 9/1997 | Lidman et al. | |
| 5,683,425 A | 11/1997 | Hauptmann | |
| 5,694,952 A | 12/1997 | Lidman et al. | |
| 5,713,938 A | 2/1998 | Chiang | |
| 5,759,199 A | 6/1998 | Snell et al. | |
| 5,899,860 A | 5/1999 | Pfeiffer et al. | |
| 5,961,540 A | 10/1999 | Renger | |
| 6,058,328 A | 5/2000 | Levine et al. | |
| 6,198,972 B1 | 3/2001 | Hartlaub et al. | |
| 6,239,724 B1 | 5/2001 | Doron et al. | |
| 6,263,249 B1 | 7/2001 | Stewart et al. | |
| 6,277,078 B1 | 8/2001 | Porat et al. | |
| 6,363,277 B1 | 3/2002 | Dooley et al. | |
| 6,372,283 B1 | 4/2002 | Shim et al. | |
| 6,409,675 B1 | 6/2002 | Turcott | |
| 6,472,991 B1 | 10/2002 | Schulman et al. | |

(Continued)

FOREIGN PATENT DOCUMENTS

EP 1471973 B1 10/2009

(Continued)

OTHER PUBLICATIONS

"International Application Serial No. PCT/US2008/013484, International Search Report mailed Mar. 27, 2009", 3 pgs.

(Continued)

*Primary Examiner* — Brian T Gedeon
(74) *Attorney, Agent, or Firm* — Schwegman, Lundberg & Woessner, P.A.

(57) ABSTRACT

An operating mode of an implantable medical device can be selected using at least one of a current or a voltage provided in response to a magnetic field sensed using a Hall effect sensor.

19 Claims, 4 Drawing Sheets

U.S. PATENT DOCUMENTS

| | | |
|---|---|---|
| 6,506,457 B2 | 1/2003 | Hum |
| 6,510,345 B1 | 1/2003 | Van et al. |
| 6,522,920 B2 | 2/2003 | Silvian et al. |
| 6,531,907 B2 | 3/2003 | Dooley et al. |
| 6,535,763 B1 | 3/2003 | Hiebert et al. |
| 6,549,811 B2 | 4/2003 | Stewart et al. |
| 6,564,100 B2 | 5/2003 | Warren et al. |
| 6,572,542 B1 | 6/2003 | Houben et al. |
| 6,574,511 B2 | 6/2003 | Lee |
| 6,580,947 B1 | 6/2003 | Thompson |
| 6,656,172 B1 | 12/2003 | Hildebrand |
| 6,662,050 B2 | 12/2003 | Olson |
| 6,704,602 B2 | 3/2004 | Berg et al. |
| 6,728,576 B2 | 4/2004 | Thompson et al. |
| 6,740,076 B2 | 5/2004 | Hoben et al. |
| 6,744,152 B2 | 6/2004 | Kroll |
| 6,745,079 B2 | 6/2004 | King |
| 6,754,526 B2 | 6/2004 | Daynes et al. |
| 6,795,732 B2 | 9/2004 | Stadler et al. |
| 6,804,558 B2 | 10/2004 | Haller et al. |
| 6,807,439 B2 | 10/2004 | Edwards et al. |
| 6,855,119 B2 | 2/2005 | Rivera et al. |
| 6,901,292 B2 | 5/2005 | Hrdlicka et al. |
| 6,920,354 B2 | 7/2005 | Daynes et al. |
| 6,928,320 B2 | 8/2005 | King |
| 6,931,281 B2 | 8/2005 | Bradley et al. |
| 6,937,906 B2 | 8/2005 | Terry et al. |
| 6,944,489 B2 | 9/2005 | Zeijlemaker et al. |
| 6,959,213 B2 | 10/2005 | Prutchi et al. |
| 6,959,214 B2 | 10/2005 | Pape et al. |
| 6,969,383 B2 | 11/2005 | Hildebrand |
| 7,001,358 B2 | 2/2006 | Fitzmaurice et al. |
| 7,016,732 B2 | 3/2006 | Warren et al. |
| 7,037,273 B2 | 5/2006 | Zhu et al. |
| 7,047,065 B2 | 5/2006 | Kalgren et al. |
| 7,050,855 B2 | 5/2006 | Zeijlemaker et al. |
| 7,052,486 B2 | 5/2006 | Hildebrand |
| 7,076,283 B2 | 7/2006 | Cho et al. |
| 7,079,977 B2 | 7/2006 | Osorio et al. |
| 7,082,328 B2 * | 7/2006 | Funke ................ 607/9 |
| 7,082,330 B2 | 7/2006 | Stadler et al. |
| 7,085,604 B2 | 8/2006 | Turney et al. |
| 7,092,759 B2 | 8/2006 | Nehls et al. |
| 7,117,037 B2 | 10/2006 | Hiebert et al. |
| 7,123,960 B2 | 10/2006 | Ding et al. |
| 7,130,681 B2 | 10/2006 | Gebhardt et al. |
| 7,146,211 B2 | 12/2006 | Frei et al. |
| 7,149,572 B2 | 12/2006 | Frei et al. |
| 7,149,773 B2 | 12/2006 | Haller et al. |
| 7,158,825 B1 | 1/2007 | Kroll et al. |
| 7,164,950 B2 | 1/2007 | Kroll et al. |
| 7,181,285 B2 | 2/2007 | Lindh et al. |
| 7,181,505 B2 | 2/2007 | Haller et al. |
| 7,203,540 B2 | 4/2007 | Ding et al. |
| 7,212,863 B2 | 5/2007 | Strandberg |
| 7,216,001 B2 | 5/2007 | Hacker et al. |
| 7,231,251 B2 | 6/2007 | Yonce et al. |
| 7,242,983 B2 | 7/2007 | Frei et al. |
| 7,272,436 B2 | 9/2007 | Gill et al. |
| 7,276,057 B2 | 10/2007 | Gerber |
| 7,280,867 B2 | 10/2007 | Frei et al. |
| 7,282,030 B2 | 10/2007 | Frei et al. |
| 7,297,114 B2 | 11/2007 | Gill et al. |
| 2003/0144704 A1 | 7/2003 | Terry et al. |
| 2005/0256503 A1 | 11/2005 | Hall |
| 2005/0256508 A1 | 11/2005 | Hall |
| 2007/0036771 A1 | 2/2007 | Wagner et al. |
| 2007/0173890 A1 * | 7/2007 | Armstrong ............ 607/2 |

FOREIGN PATENT DOCUMENTS

| | | |
|---|---|---|
| WO | WO-2009/075814 A1 | 6/2009 |

OTHER PUBLICATIONS

"International Application Serial No. PCT/US2008/013484, International Written opinion Mailed Mar. 27, 2009", 7 pgs.

* cited by examiner

IMPLANTABLE MEDICAL DEVICE WITH HALL SENSOR

CLAIM OF PRIORITY

This patent application claims the benefit of priority, under 35 U.S.C. Section 119(e), to William J. Linder et al., U.S. Provisional Patent Application Ser. No. 61/007,455, entitled "CARDIAC RHYTHM MANAGEMENT DEVICE WITH HALL SENSOR," filed on Dec. 12, 2007, incorporated herein by reference in its entirety.

BACKGROUND

An implantable medical device (IMD) can be used to monitor one or more tissue sites or to provide electrostimulation to one or more tissue sites such as to elicit or inhibit a contractile response in muscle tissue, or to provide one or more other forms of electrostimulation (e.g., a neural stimulation, such as directed to a vagal site, such as for pain management, to provide a therapy for one or more heart arrhythmias, or for one or more other therapeutic or diagnostic uses). For example, spontaneous intrinsic depolarizations can be generated by a heart itself, while evoked intrinsic depolarizations can be the result of an electrostimulation pulse such as a pacing pulse. Depolarization of heart tissue can cause it to contract. After contraction, while a heart chamber is expanding to fill with blood, repolarization of the heart tissue can occur allowing subsequent depolarization. An implantable medical device such as a cardiac rhythm management device (CRMD) can deliver electrostimulation pulses to regulate such heart tissue contraction. Examples of a cardiac rhythm management device can include, among other things, a pacemaker, a defibrillator, a cardioverter, a cardiac resynchronization device, or one or more other devices combining some or all such capabilities or one or more other capabilities.

Also, cardiac rate, contractility and excitability can be modulated through central nervous system mediated reflex pathways, which can include portions of the sympathetic and parasympathetic components of the autonomic nervous system. For example, baroreceptors and chemoreceptors in the heart, great vessels, and lungs can transmit cardiac activity information through parasympathetic and sympathetic afferent nervous fibers to the central nervous system. Increase of sympathetic afferent activity can trigger reflex sympathetic activation, parasympathetic inhibition, blood vessel constriction, and tachycardia. In contrast, parasympathetic activation can result in bradycardia, blood vessel dilation, and inhibition of vasopressin release.

The balance between the sympathetic and parasympathetic components of the autonomic nervous system can be referred to as the autonomic tone. Decreased parasympathetic or vagal tone can be a factor that can contribute to or cause various cardiac tachyarrhythmias. Such tachyarrhythmias can include atrial fibrillation and ventricular tachycardia, for example. In an example, an implantable medical device can deliver neural stimulation, such as to elicit the reflex response of parasympathetic activation or of sympathetic inhibition. In certain examples, the neural stimulation can include one or more of magnetic, electrical, optical or acoustic stimulation of neural targets.

OVERVIEW

In an example, a Hall effect sensor can be formed as a portion of an integrated circuit that can include a processor. In an example, an integrated Hall effect sensor can be used to sense the presence of a magnetic field and to provide signal for use in selecting a cardiac therapy mode. In an example, the polling rate of the Hall effect sensor can be adjusted after sensing a magnetic field. In an example, the Hall effect sensor can provide provides a measure of the strength of a magnetic field near an implantable medical device.

In Example 1, an apparatus includes an implantable medical device, the implantable medical device including a Hall effect sensor configured to sense a magnetic field and to provide at least one of a current or a voltage in response to the magnetic field, and a processor electrically coupled to the Hall effect sensor, the processor configured to select an operating mode of the implantable medical device using at least one of the current or the voltage provided by the Hall effect sensor.

In Example 2, the Hall effect sensor of Example 1 is optionally configured to adjust at least one of the current or the voltage provided in response to the magnetic field, and the processor of Example 1 is optionally configured to select the operating mode of the implantable medical device in response to the adjustment of the at least one of the current or the voltage.

In Example 3, the processor of any one or more of Examples 1-2 is optionally configured to select the operating mode of the implantable medical device from a list including at least one of (1) a first operating mode when a magnitude of the magnetic field is below a specified first threshold, (2) a second operating mode when the magnitude of the magnetic field exceeds or equals the specified first threshold over a specified first duration, or (3) a third operating mode when the magnitude of the magnetic field further exceeds or equals a specified second threshold over a specified second duration.

In Example 4, the first operating mode of any one or more of Examples 1-3 optionally includes an ambulatory operating mode, the second operating mode of any one or more of Examples 1-3 optionally includes a battery status test mode wherein the implantable medical device is configured to provide an indication to a user corresponding to a battery status, and the third operating mode of any one or more of Examples 1-3 includes a magnetic resonance imaging (MRI) safe mode.

In Example 5, the Hall effect sensor of any one or more of Examples 1-4 is optionally rotationally symmetric about an axis.

In Example 6, the Hall effect sensor of any one or more of Examples 1-5 optionally comprises an integrated circuit.

In Example 7, the integrated circuit of any one or more of Examples 1-6 optionally includes a heterostructure configured to increase a Hall mobility associated with the Hall effect sensor.

In Example 8, the processor and the Hall effect sensor of any one or more of Examples 1-7 are both included optionally in a commonly shared integrated circuit package.

In Example 9, the processor and the Hall effect sensor of any one or more of Examples 1-8 are both included optionally in a commonly shared integrated circuit.

In Example 10, the implantable medical device of any one or more of Examples 1-9 optionally includes a polling circuit electrically coupled to the Hall effect sensor, the polling circuit configured to provide an excitation voltage to the Hall effect sensor, and optionally includes an analog-to-digital converter electrically coupled to the Hall effect sensor and configured to measure at least one of the current or the voltage provided by the Hall effect sensor in response to the magnetic field.

In Example 11, the processor of one or more of Examples 1-10 is optionally configured to control one or more excitation parameters associated with the polling circuit, the one or more parameters comprising at least one of (1) an excitation amplitude, (2) an excitation pulse width, (3) a timing between one or more excitation pulses, or (4) an excitation contact for delivery of the excitation voltage.

In Example 12, the Hall effect sensor and at least one of the polling circuit or the analog-to-digital converter of any one or more of Examples 1-11 are included optionally in a commonly shared integrated circuit.

In Example 13, a method includes sensing a magnetic field using a Hall effect sensor, providing at least one of a current or a voltage in response to the magnetic field, and selecting an operating mode of an implantable medical device using at least one of the current or the voltage.

In Example 14, the providing at least one of the current or the voltage of Example 13 optionally includes using the Hall effect sensor, the method of Example 13 optionally includes monitoring at least one of the current or the voltage, and the selecting the operating mode of the implantable medical device of Example 13 optionally occurs at least in part in response to the monitoring at least one of the current or the voltage.

In Example 15, the method any one or more of Examples 13-14 optionally includes sensing a magnitude of the magnetic field using the Hall effect sensor, comparing the sensed magnitude of the magnetic field to at least one of a specified first threshold or a specified second threshold, and selecting, in response to the comparing, the operating mode of the implantable medical device from a list including at least one of (1) a first operating mode when the magnitude of the magnetic field is below the specified first threshold, (2) a second operating mode when the magnitude of the magnetic field exceeds or equals the specified first threshold over a specified first duration, or (3) a third operating mode when the magnitude of the magnetic field further exceeds or equals the specified second threshold over a specified second duration.

In Example 16, the selecting the first operating mode of any one or more of Examples 13-15 optionally includes selecting an ambulatory operating mode, the selecting the second operating mode of any one or more of Examples 13-15 optionally includes selecting a battery status test mode and optionally includes providing an indication to a user corresponding to a battery status, and the selecting the third operating mode of any one or more of Examples 13-15 optionally includes selecting a magnetic resonance imaging (MRI) safe mode.

In Example 17, the method of any one or more of Examples 13-16 optionally includes exciting the Hall effect sensor using a polling circuit configured to provide an excitation voltage to the Hall effect sensor, and the monitoring at least one of the current or the voltage of any one or more of Examples 13-16 optionally includes using an analog-to-digital converter electrically coupled to the Hall effect sensor.

In Example 18, the method of any one or more of Examples 13-17 optionally includes controlling one or more excitation parameters associated with the exciting the Hall effect sensor, the one or more excitation parameters optionally including at least one of (1) an excitation amplitude, (2) an excitation pulse width, (3) a timing between one or more excitation pulses, or (4) an excitation contact for delivery of the excitation voltage.

In Example 19, the method of any one or more of Examples 13-18 optionally includes sensing a magnitude of the magnetic field using the Hall effect sensor, comparing the sensed magnitude to a specified magnitude window, and increasing, in response to the comparing, the timing between one or more excitation pulses when the sensed magnitude is within the specified window throughout a specified duration.

In Example 20, the method of any one or more of Examples 13-19 optionally includes sensing a magnitude of the magnetic field using the Hall effect sensor, comparing a sensed magnitude of the magnetic field to a specified magnitude window, and limiting, in response to the comparing, the number of excitation pulses over a specified first duration when the sensed magnitude is within the specified window throughout a specified second duration.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In an example, energy delivered by electrostimulation pulses can be supplied by a battery located within the implantable medical device, such as a cardiac rhythm management device or one or more other implantable medical devices. In this example, the energy stored in the battery can decrease over time, such as due to normal operation of the implantable device, with the delivery of electrostimulation pulses, or due to one or more other effects. In an example, a user can be provided with an indication to estimate the remaining life of the battery in the implantable medical device, such as the cardiac rhythm management device, such as by switching to a battery status test mode and observing a pacing pulse rate of pulses that are issued as a function of the battery's terminal voltage or one or more other indicators of the remaining battery life (e.g., a state of charge).

A mechanical switch can be responsive to a magnetic field, such as a "reed switch," and can be used to place the cardiac rhythm management device into such a battery status test mode. The mechanical switch can also respond to one or more other magnetic fields that are not applied in relation to cardiac therapy.

A sufficiently large magnetic field can interfere with the delivery of electrostimulation pulses, such as by inadvertently placing the cardiac rhythm management device into one of one or more non-therapy or reduced-therapy modes, such as a test mode, a factory preset mode where therapy is disabled, a safety or fallback mode providing more limited therapy, or one or more other modes. If the magnetic field is very large, for example, as with magnetic fields generated during a magnetic resonance imaging procedure, abnormally large electrical currents can flow in the circuit conductors, abnormally large physical forces can be experienced by circuits containing magnetic materials, or one or more other undesirable effects can occur. Such abnormally large currents can cause excessive internal heating to occur and can damage the internal components of the cardiac rhythm management device. Similarly, the abnormally large forces experienced by the circuits containing magnetic materials can result in temporary impairment or permanent damage to the cardiac rhythm management device.

The present inventors have recognized, among other things, that a solid-state magnetic field sensor responsive to the presence of magnetic fields can be used in place of, or in addition to, a magnetically operated mechanical switch. In an example, a solid-state magnetic field sensor can also be used to characterize the strength (e.g., magnitude or one or more other parameters) of a sensed magnetic field. In certain examples, the solid-state magnetic sensor can be configured to recognize magnetic fields that are associated with one or more therapies, including a cardiac therapy, and to distinguish such magnetic fields from other magnetic fields without requiring moving parts. Thus, a solid-state magnetic sensor can be used to place the cardiac rhythm management device into the battery status test mode, such as to induce an alternative mode of electrostimulation, or into a magnetic resonance imaging (MRI) safe mode to reduce the likelihood of internal damage during exposure to an abnormally large externally-applied magnetic field, or one or more other operating modes.

Figure 1:
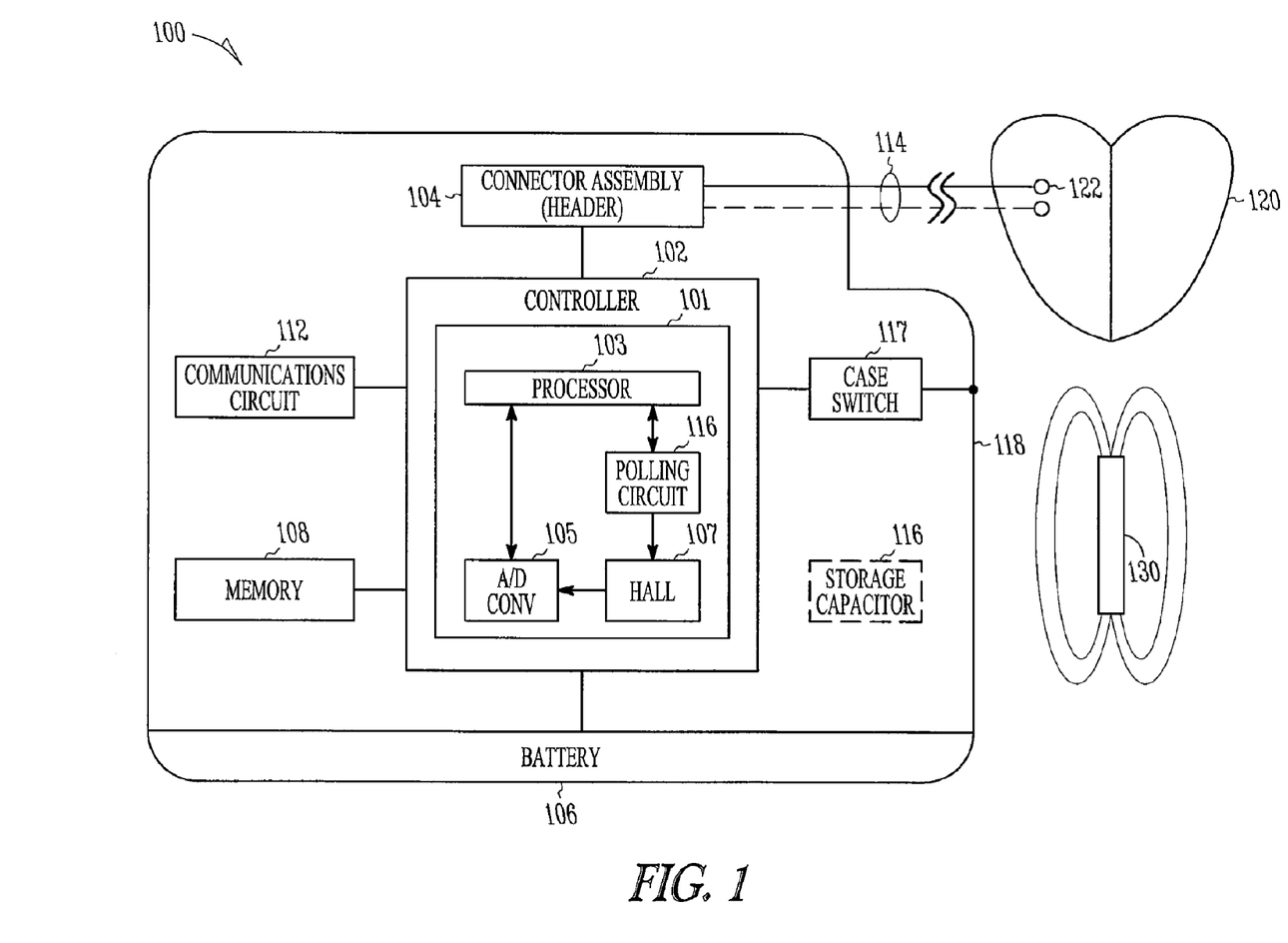
FIG. 1 shows an example of a portion of an implantable cardiac rhythm management device.

FIG. 1 illustrates an example of a portion of an implantable cardiac rhythm management device 100, such as for delivering electrostimulation to, or sensing spontaneous intrinsic or evoked depolarizations from, a desired portion of a heart 120. In this example, the cardiac rhythm management device 100 can include a controller module 102, a connector assembly 104, a battery 106, a memory unit 108, communications circuitry 112, a case switch 117, and an energy storage capacitor 116 located within casing 118. In this example, the controller module 102 can include an integrated circuit module 101 with a processor 103, an analog-digital circuit 105, a polling circuit 116, and a Hall effect sensor 107. In an example, electrostimulation pulses can be derived from the energy storage capacitor 116 and delivered to one or more heart chambers, such as via one or more electrodes 122, which can be associated with one or more leads 114. In an example, the polling circuit 116 can be used to provide excitation current or excitation voltage signals to the Hall effect sensor 107. In certain examples, the polling circuit 116 can include a timing circuit or can be configured to receive one or more timing control signals from the processor 103. As will be explained below, the Hall effect sensor 107 can be used to sense the presence and the strength of a magnetic field, such as originating from an external magnetic device, such as a magnetic device 130 (e.g., a permanent magnet, an electromagnet, a static or dynamic magnetic field from one or more pieces of diagnostic medical apparatus such as a magnetic resonance imaging (MRI) scanner, or one or more other sources of the magnetic field). In certain examples, the magnetic device 130 can include a magnet intentionally placed near the cardiac rhythm management device 100 by a user, or another device capable of generating a magnetic field of sufficient strength to trigger a change from the normal ambulatory operating mode, such as by placing the cardiac rhythm management device in a battery status test mode, a mode configured to abort therapy delivery, a mode to trigger storage of electrograms containing physiologic information derived from one or more tissue sites, a mode to trigger one or more research features, a mode to increase or decrease therapy, or one or more other operating modes. In an example, the signals generated by the Hall effect sensor 107 in the presence of a magnetic field can also be used by the processor 103 to select between one or more pacing, defibrillation, or one or other operating modes. In this example, such modes can be programmed into a memory unit 108. In certain examples, the integrated circuit module 101 can include a semiconductor memory, such as a flash memory, NMOS, SRAM, DRAM, EPROM, EEPROM, or one or more other forms of semiconductor memory to store instructions or data, such as associated with a cardiac therapy.

In certain examples, one or more of the processor 103, the analog-digital circuit 105, the polling circuit 116, or the Hall effect sensor 107 can be formed monolithically and integrated together on a single commonly shared substrate, such as silicon, silicon-on-insulator, silicon-on-sapphire, silicon carbide, silicon germanium, silicon germanium carbide, gallium arsenide, gallium nitride, indium phosphide, diamond, or one or more other substrate materials included as a portion, part, or component of a commonly shared integrated circuit or a commonly shared integrated circuit package. In certain examples, one or more of the processor 103, the analog-digital circuit 105, the polling circuit 116, or the Hall effect sensor 107 can be included as a portion, part, or component of an integrated circuit package (e.g., a plastic-encapsulated ball grid array (BGA), flip-chip, land grid array (LGA), tape-automated bonding (TAB), or one or more other types of an integrated circuit package).

In certain examples, a portion of the integrated circuit module 101 can include circuits formed of different materials. For example, the Hall effect sensor 107 can be formed as a separate die and attached to the integrated circuit module 101 via solder bump mounting technology, flip-chip technology, or one or more other packaging, mounting, or assembly techniques. The Hall Effect sensor 107 can also be formed directly on the integrated circuit module 101 by a semiconductor or other manufacturing process, such as chemical vapor deposition. Thus, the Hall effect sensor 107 can include a semiconductor material that is different than the semiconductor material used for forming the processor 103, the analog-digital circuit 105, or the polling circuit 116, or one or more other circuits included as a portion of the integrated circuit module 101 or one or more other modules. In certain examples, one or more materials with higher Hall mobilities, such as indium antimonide, gallium antimonide, or one or more other materials can be selected to enhance sensitivity of the Hall effect sensor 107 to a magnetic field.

The Hall effect sensor 107 can be formed as a heterostructure device including adjoining layers having one or more bandgap energies different from an adjoining layer to confine current flow. Layers with different bandgap energies can be obtained, for example, with III-VI and III-V compound semiconductors, such as aluminum gallium arsenide-gallium arsenide, indium phosphide-indium gallium arsenide, or one or more other compound semiconductors.

The cardiac rhythm management device 100 shown is for ease in understanding the examples described, and is not meant to limit device 100 to the particular configuration illustrated. For example, the communications circuit 112 and the memory 108 can be are formed monolithically with the processor 103 as a portion of the integrated circuit module 101, and can be included in the cardiac rhythm management device 100 along with one or more other circuits or modules. In an example, the timing circuit can be included as a portion of the processor 103 or the analog-to-digital circuit 105.

Figure 2A:
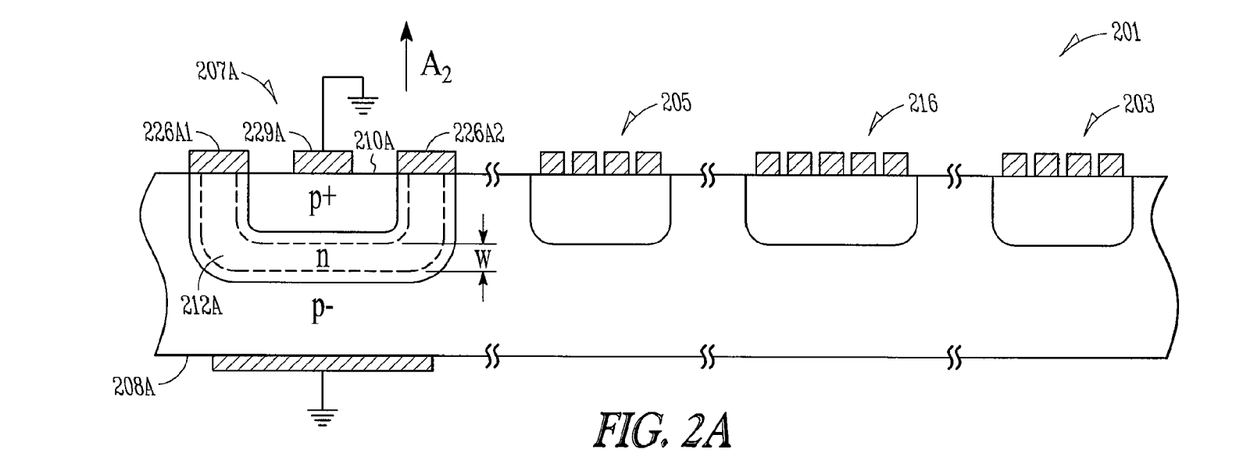
FIGS. 2A-B show examples of an integrated circuit structure for an implantable cardiac rhythm management device.
Figure 2B:
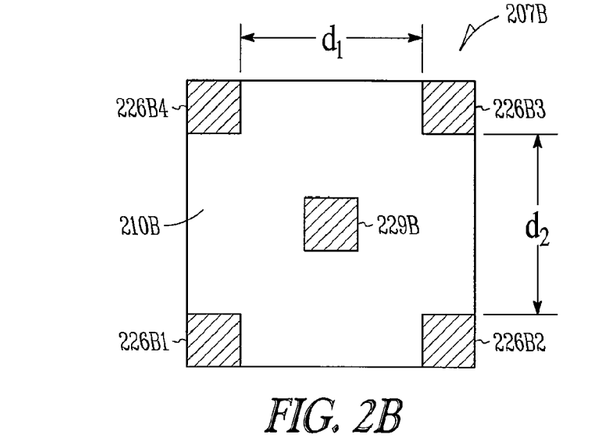

FIGS. 2A-B show examples of an integrated circuit structure for an implantable cardiac rhythm management device, such as cardiac rhythm management device 100. Illustrated in FIG. 2A is a cross-sectional view of a portion of a monolithic integrated circuit module 201 that can include a Hall effect sensor 207A, an analog-to-digital circuit 205, a polling circuit 216, and a processor 203. In an example, the analog-to-digital circuit 205 is an analog-to-digital converter. FIG. 2B is a planar view of a Hall effect sensor 207B with a square geometry. In an example, the Hall effect sensor 207A-B, like the processor 203A, the analog-digital circuit 205A, and the polling circuit 216A, can be patterned, such as by a photolithographic process, as part of a process to form an integrated circuit module. Therefore, other Hall effect sensor geometries are possible, such as one having the shape of a cruciform pattern, or one or more other patterns. In various examples, Hall effect sensor 207A and Hall effect sensor 207B are the same sensor.

In an example, the polling circuit 216 can be configured to apply voltages or other signals to the Hall effect sensor 207A-B. In an example, the analog-to-digital circuit 205 can be configured to receive one or more current or voltage signals from the Hall effect sensor 207, such as in response to one or more voltage signals applied by the polling circuit 216, and to convert the received signals to digital signals. In an example, analog-to-digital circuit 205 provides a 12-bit voltage signal to processor 203, such for use in determining the existence or strength of a magnetic field. In an example, the processor 203 can also use the digital signals provided by the analog-to-digital circuit 205 to estimate a magnetic field strength near the cardiac rhythm management device 100. In an example, the processor 203 can also use the estimated magnetic field strength (e.g., a magnitude of the magnetic field) derived from the digital signals provided by the analog-to-digital circuit 205, along with one or more programmable thresholds or windows, to select an operating mode of the cardiac rhythm management device 100.

In certain examples, the Hall effect sensor 207A includes an n-well 209A formed within a p-region 208A. A p-region 210A can be formed in the n-well 209A, such as to define a buried n-channel with a width (w), thereby limiting the flow of electrons to a non-depleted region 212A between a first contact 226A1 and a second contact 226A2. In an example, the p-region 208A and the p-region 210A can be coupled to a reference potential, such as circuit ground, to regulate conduction in the buried n-channel through use of the respective depletion widths to adjust width (w). The n-well 209A and the p-region 210A can be formed by ion implantation or diffusion in certain examples. In various examples, the carrier density in the n-well 209A can be from about $10^{15}$ cm$^{-3}$ to about $10^{17}$ cm$^{-3}$. The dimension of the n-well 209A between the p-region 208A and the p-region 210A can range from about 1 micrometers to about 3 micrometers, in certain examples. In certain examples, the depth of the p-region 210A can be between about 0.1 micrometers and about 1 micrometers and can have a carrier density of greater than $5 \times 10^{17}$ cm$^{-3}$. The carrier density in the p-region 208A can be on the order of $10^{15}$ cm$^{-3}$. In various examples, the p-region 208A is a region of a substrate, which can be fabricated to be isolated from the processor 203, the analog-to-digital circuit 205, or the polling circuit 216, or from one or more other circuits.

The Hall effect sensor 207A-B can be a rotationally symmetric structure, such as shown in the example of FIG. 2B. A rotationally symmetric structure can have a near zero offset voltage, thereby reducing the number of measurements used for accurately sensing the presence of a magnetic field near the cardiac rhythm management device 100. The current density in the non-depleted portion 212A can be represented by $$J = q^2 n/m^* <\tau_m/(1+(\omega_c \tau_m)^2)> E - q^3 n/m^{*2} <\tau^2_m/(1+(\omega_c \tau_m)^2)>(E \times B) + q^4 n/m^{*3} <\tau^3_m/(1+(\omega_c \tau_m)^2)> B (E \cdot B) \qquad (1)$$

where J represents a current density vector, E represents an electric field vector, B represents a magnetic field vector, q represents an electric charge, n represents a conduction band carrier density in the non-depleted region 212A, $\tau_m$ represents a momentum relation time, m* represents an effective mass of the carriers in the conduction band, $\omega_c$ represents a cyclotron frequency, and <> denotes the average of the values given by the variables contained therein. The first term can be associated with the Hall effect, the second and third terms can be associated with a magnetoresistance effect. Equation 1 can enable a magnetic field to be sensed with a semiconductor by one or more current or voltage measurements. If a suitable geometry is selected for the Hall effect sensor, the calculation for sensing a magnetic field can be simplified.

In an illustrative example, if the magnetic flux gradient does not vary across the non-depleted portion 212A, the magnetic field vector (represented by $\hat{A}_z$) can be substantially uniformly normal to the surface of the Hall effect sensor. This can occur where the size of the Hall effect sensor can be made small in relation to the associated magnetic flux lines. If also the magnetic field strength can be such that the magnetoresistance terms are small in relation to the Hall effect term, and the current density in the y-direction can be near zero, the current density vector J can be approximated by $$J_x = -qn/B_z <\tau_m>^2/<\tau_m^2> E_y \qquad (1)$$

and the Hall constant $R_H$ can be approximated by $$R_H = -\frac{E_y}{(J_x B_z)} = -1/(qn)<\tau_m^2>/<\tau_m>^2 \qquad (3)$$

where the Hall factor can be represented by $$r_H = <\tau_m^2>/<\tau_m>^2. \qquad (4)$$

For a lightly doped non-depleted region 212A, such as given above, $r_H$ can be close to unity and the Hall mobility can be represented by $$\mu_H = R_H \sigma = q^2 n <\tau_m>/m^* = \mu_n r_H, \qquad (5)$$

where σ represents a conductivity of the carriers in the non-depleted region 212A and $\mu_n$ represents an associated conduction band carrier mobility. The above geometric constraints can be obtained by applying a magnetic field substantially in the z-direction, measuring voltage in the y-direction, and measuring current in the x-direction. Thus, in this illustrative example, the magnetic field can be represented by, $$B_z = -qn(E_y/J_x) r_H. \qquad (6)$$

Therefore, the measurements of a voltage or a current signal made with the Hall sensor 207A-B can be used by the processor 203 to estimate magnetic field strength as well as to identify its presence. Accordingly, in certain examples, the Hall effect sensor 207A-B can be used to switch a cardiac rhythm management device into one or more different operating modes, such as a battery status test mode, or an MRI-safe mode, such as depending on differing degrees of magnetic field strength that can be present. In an example, the Hall effect sensor can also enable near real time adjustments to the delivery of cardiac therapy upon sensing a magnetic field that can interfere with delivery of electrostimulation pulses (e.g., inhibiting, increasing, decreasing or otherwise adjusting the therapy).

The Hall factor can be responsible for causing significant measurement error, and therefore, it can be taken into consideration. The error can be reduced, but a tradeoff can exist in terms of added complexity and battery energy expended in performing the relevant calculations. In an illustrative example, a correction can be generated by making a series of eight voltage-current measurements, averaging pairs of measured voltages, generating offset voltage coefficients, and generating a geometric correction factor by either an algorithm or a lookup table. The present inventors have also recognized that for a rotationally symmetric structure such as shown in FIG. 2B, the offset voltage can be reduced to nearly zero and fewer voltage measurements (e.g., two instead of eight) can be used to more accurately identify the presence and strength (such as a magnitude) of a magnetic field without requiring more complex calculations. The geometric correction factor can also be unity for a rotationally symmetric geometry, thereby substantially reducing the geometric factor as a source of measurement error.

Although the Hall effect sensor 207A-B is illustrated in FIGS. 2A-B as having n-type conduction, p-type conduction can also be used to sense a magnetic field. In such an example, p-type carriers can substituted for the n-type carriers in the n-well 209A, and the n-type carriers for the p-type carriers in the p-region 208A and the p-region 210A. In doing so, the resulting Hall constant will undergo a sign change, which need not affect sensing a magnetic field using Hall effect sensor. In an example, a Hall effect sensor can also be formed without a p-region 210A by placing metal 229B in direct contact with n-well 209A thereby forming a Schottky contact structure, or by substituting a suitable oxide for the p-region 210A forming a metal-oxide-semiconductor contact structure.

Figure 3:
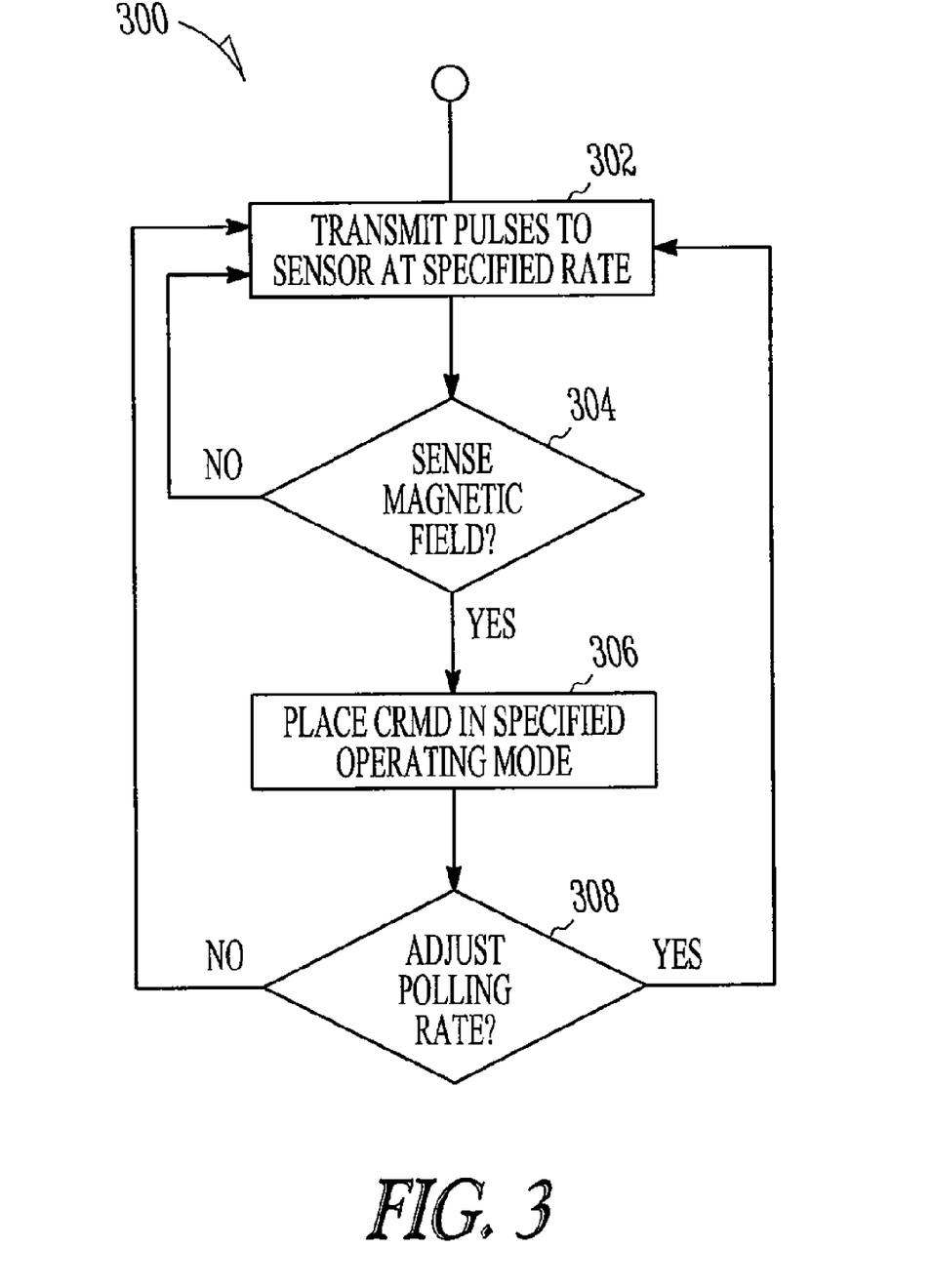
FIG. 3 shows an example of a method for sensing a magnetic field near an implantable cardiac rhythm management device.

FIG. 3 shows an example of a method 300 for sensing a magnetic field near an implantable cardiac rhythm management device. At 302 a polling circuit, such as circuit 116 and 216, can apply one or more voltage pulses between a first contact 226B1 and a third contact 226B3, or between a second contact 226B2 and a fourth contact 226B4 of Hall effect sensor 207B thereby generating a current flow between two or more contacts. At substantially the same time, a voltage can be measured between the two diagonally located contacts that do not need to receive the voltage pulses. In an illustrative example, the applied voltage can have a excitation magnitude of about 2.2 Volts. The voltage pulses can be applied periodically with a low duty cycle (e.g., an excitation pulse width) to reduce the amount of power consumed to during a sensing interval. In certain examples, the voltage pulses are periodically applied to the Hall effect sensor at a rate of about 1-2 per second (e.g., an excitation pulse repetition rate) with a pulse width of about 20-40 microseconds. The current flowing between the contacts and the voltage generated across the contacts can be transmitted to an analog-to-digital circuit, such as analog-to-digital circuit 105 and 205 for further processing. The analog-to-digital circuit can output a digitized representation of the analog signals received from the Hall effect sensor to a processor, such as processor 103 and 203.

At 304 the processor determines whether a measurable magnetic field is present, such as by comparing a sensed magnitude of the magnetic field with one or more programmable thresholds, and determining that the magnetic field is present when the sensed magnitude equals or exceeds the one or more programmable thresholds. If the magnetic field is not sensed, the polling circuit continues to apply voltage pulses the contacts of the Hall effect sensor at the specified rate. The one or more programmable thresholds can be used so that the processor does not operate on signals provided by the Hall effect sensor corresponding to a weaker magnetic field, such as due to a normal background magnetic field, to conserve battery energy.

At 306, operation of the cardiac rhythm management device can be placed in a specified operating mode, such as a battery status test mode, an MRI-safe mode, or one or more other modes of cardiac therapy upon sensing the magnetic field. Switching between operating modes can occur in near real time with the measurement of magnetic field. In certain examples, the operating mode can be selected according to the strength (e.g., magnitude) of the magnetic field. In an example, the operating mode is selected to adjust delivery of a cardiac therapy in response to the sensed strength of the magnetic field.

In some examples, the operating mode need not change in response to sensing the magnetic field where the field's strength has not changed substantially from the prior strength measurement, or where the strength of the magnetic field is within a specified range or zone. In certain examples, the operating mode of the cardiac rhythm management device does not change in response to the magnetic field where the strength of the field is below a sensing threshold.

At 308, the polling rate of the Hall effect sensor can be increased or decreased in response to the detection of the magnetic field. In certain examples, the processor communicates a signal to the polling circuit to increase the rate of application of voltage pulses to the Hall effect sensor. In certain examples, a timing circuit can be used to signal the polling circuit to change the rate of application of voltages pulses. In an illustrative example, an increased rate of application of voltage pulses is about 20 per second. The timing circuit can be configured to increase, decrease and reset the rate the at which voltage pulses are applied to the Hall effect sensor. As such, the timing circuit can be used as a window timer to limit a total number of voltage pulses that can be applied during a specified time period in response to sensing the magnetic field. For example, where a switching magnet is inadvertently left near a patient's cardiac rhythm management device by a clinician.

At 308 the rate of application of voltages pulses to the Hall effect sensor can continue at the increased rate until the magnetic field is no longer sensed, or the strength is less than or equal to a specified value or threshold.

In an example, if the magnetic field is no longer sensed, the processor signals the polling circuit to reduce the rate of application of voltage pulses to the Hall effect sensor. In certain examples, the polling rate is returned the rate used before the magnetic field was sensed. In such examples, the polling circuit can continue to apply voltage pulses to the Hall effect sensor at a decreased rate until the magnetic field can be again sensed.

Figure 4A:
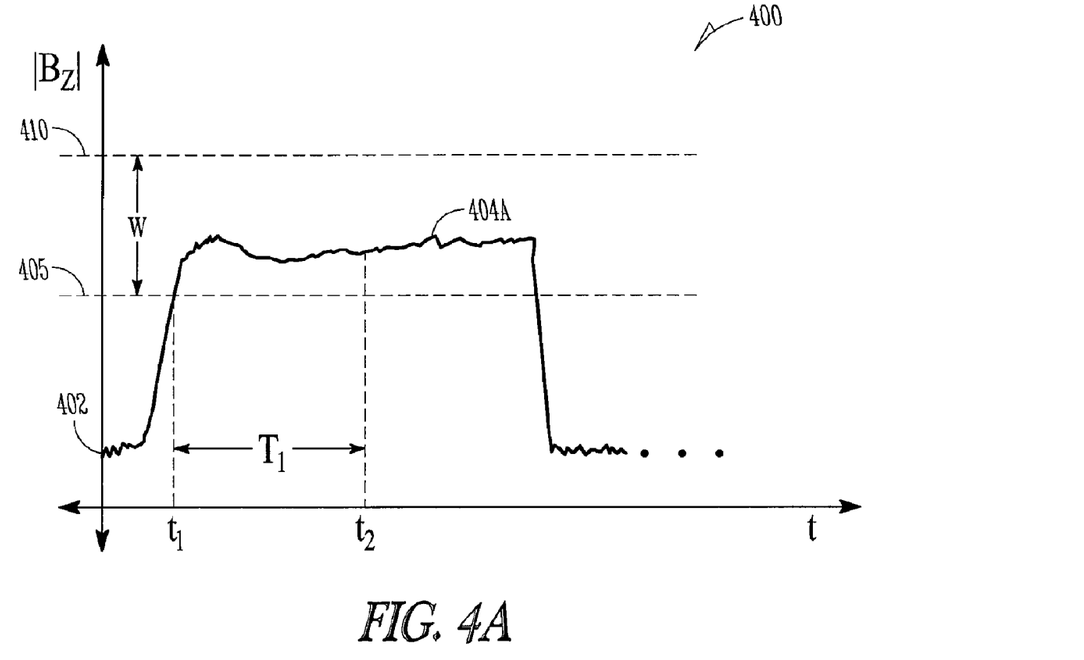
FIG. 4A-B show illustrative examples of a plot of a magnetic field magnitude versus time with respect to one or more device thresholds or time intervals.
Figure 4B:
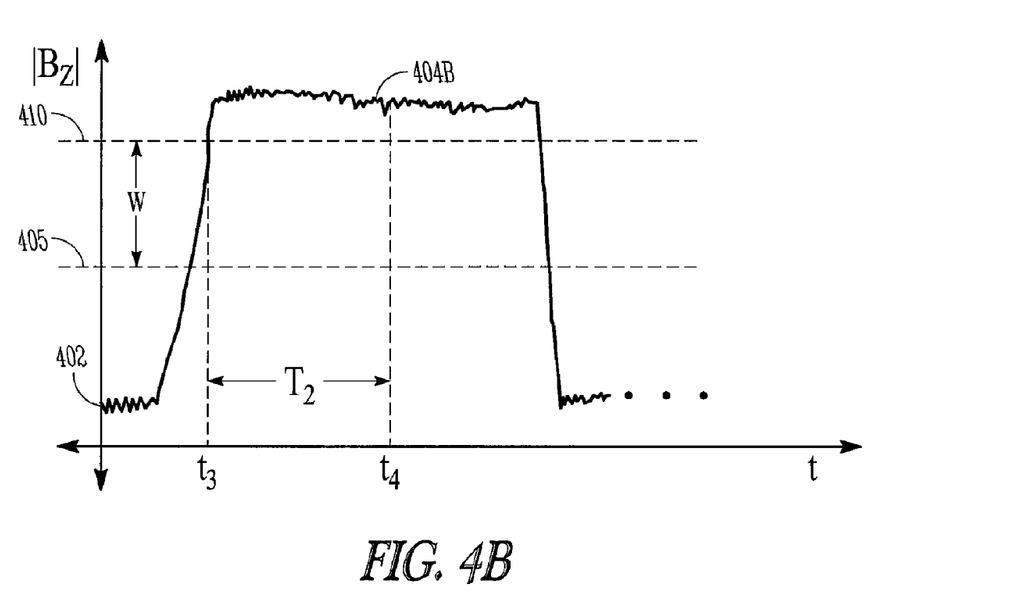

FIGS. 4A-B show illustrative examples of a plot 400 of a sensed magnitude of a magnetic field 402 versus time ("t") with respect to one or more programmable thresholds or programmable time intervals associated with a cardiac rhythm management device 100. In the example shown in FIG. 4A, at a time $t_1$, the magnetic field 402 can cross a first threshold 405, and can be between the first threshold 405 and a second threshold 410 (e.g., corresponding to a threshold window "w" as shown) according to information provided by a magnetic sensor such as a Hall effect sensor 107. In an example, a timer can be started and if at time $t_2$, throughout a first specified duration such as an interval $T_1$, the magnetic field 402 is still equal to or exceeding the first threshold 405, then a different operating mode of the cardiac rhythm management device 100 can be selected. In an example, a change from an ambulatory operating mode to another operating mode such as a battery status test mode, or an MRI-safe mode, or one or more other modes, can occur when the magnetic field 402 is within the amplitude window "w" throughout the first interval $T_1$. In an example, a first elevated magnetic field level 404A can be caused by an placement of an external permanent magnet near the cardiac rhythm management device 100 (e.g., by a user such as a patient, or a physician, or one or more others to elicit a battery status indication).

In the example of FIG. 4B, the magnetic field 402 can cross the second threshold 410 at time $t_3$ and can continuously equal or exceed the second threshold 410 throughout a second specified duration, such as a second interval $T_2=t_4-t_3$. In an example, a second elevated magnetic field level 404B can be caused by an external magnetic field having a larger magnitude than the first elevated magnetic field level 404B being near the cardiac rhythm management device 100. In certain examples, the larger magnitude magnetic field can be caused by a static or dynamic magnetic field associated with a diagnostic medical imaging procedure such as magnetic resonance imaging (MRI), by heavy equipment such as welding, electrical control or switching equipment, or motors, or by one or more other sources. In an example, the cardiac rhythm management device 100 can select one or more operating modes to inhibit therapy, prevent over-sensing, or respond in one or more other ways to prevent inadvertent or unwanted changes in the operation of the cardiac rhythm management device 100 in the presence of the second elevated magnetic field level 404 above or equal to the second threshold 410 over a duration of $T_2$.

In an example, a processor 103, such as shown in FIG. 1, can be part of a cardiac rhythm management device including one or more magnetic sensors. In this example, the processor 103 can include one or more comparators, and can be used to compare the magnetic field 402 to one or more thresholds such as the first threshold 405 or the second threshold 410, such as by using a digital representation of the magnetic field provided by an analog-to-digital converter 105. In an example, the processor 103 can include or control one or more timers to measure intervals such as the first interval $T_1$, second interval $T_2$, or one or more other intervals. In an example, the processor 103 can select one or more operating modes using the one or more comparators or timers and using one or more thresholds or intervals, such as shown in FIG. 4.

In certain examples, the Hall effect sensor 107 can be a portion, part, or component included in one or more other implantable medical devices. The one or more other implantable medical devices can include an implantable patient monitor, a neural stimulation device, or one or more other implantable medical devices configured to monitor one or more tissue sites or to provide electrostimulation to one or more tissue sites. The one or more other implantable medical devices can include one or more components, parts or portions shown in FIG. 1 and discussed in relation to the cardiac rhythm management device 100.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable medical device including:

a Hall effect sensor configured to sense a magnetic field and to provide at least one of a current or a voltage in response to the magnetic field;

a processor electrically coupled to the Hall effect sensor, the processor configured to select an operating mode of the implantable medical device using at least one of the current or the voltage provided by the Hall effect sensor;

a polling circuit electrically coupled to the Hall effect sensor and configured to provide an excitation current to the Hall effect sensor; and an analog-to-digital converter electrically coupled to the Hall effect sensor and configured to measure at least one of the current or the voltage provided by the Hall effect sensor in response to the magnetic field; and wherein the Hall effect sensor and the polling circuit are included in a commonly-shared semiconductor integrated circuit.

2. The apparatus of claim 1, wherein the Hall effect sensor is configured to adjust at least one of the current or the voltage provided in response to the magnetic field; and wherein the processor is configured to select the operating mode of the implantable medical device in response to the adjustment of the at least one of the current or the voltage.

3. The apparatus of claim 1, wherein the processor is configured to select the operating mode of the implantable medical device from a list including at least one of:

(1) a first operating mode when a magnitude of the magnetic field is below a specified first threshold;

(2) a second operating mode when the magnitude of the magnetic field exceeds or equals the specified first threshold over a specified first duration; or (3) a third operating mode when the magnitude of the magnetic field further exceeds or equals a specified second threshold over a specified second duration.

4. The apparatus of claim 3, wherein the first operating mode includes an ambulatory operating mode;

wherein the second operating mode includes a battery status test mode wherein the implantable medical device is configured to provide an indication to a user corresponding to a battery status; and wherein the third operating mode includes a magnetic resonance imaging (MRI) safe mode.

5. The apparatus of claim 1, wherein the Hall effect sensor is rotationally symmetric about an axis.

6. The apparatus of claim 1, wherein the integrated circuit includes a heterostructure configured to increase a Hall mobility associated with the Hall effect sensor.

7. The apparatus of claim 1, wherein the processor is configured to control one or more excitation parameters associated with the polling circuit, the one or more parameters comprising at least one of:

(1) an excitation amplitude;
(2) an excitation pulse width;
(3) a timing between one or more excitation pulses; or
(4) an excitation contact for delivery of the excitation current.

8. The apparatus of claim 1, wherein the Hall effect sensor and at least one of the processor or the analog-to-digital converter are included in the commonly shared semiconductor integrated circuit.

9. A method comprising:

exciting a Hall effect sensor using a polling circuit configured to provide an excitation current to the Hall effect sensor, the polling circuit and the Hall effect sensor included in a commonly-shared semiconductor integrated circuit;

sensing a magnetic field using a Hall effect sensor, including monitoring at least one of a current or a voltage provided by the Hall effect sensor in response to the sensed magnetic field; and in response, selecting an operating mode of an implantable medical device using information provided by the monitoring at least one of the current or the voltage; and wherein the monitoring at least one of the current or the voltage includes using an analog-to-digital converter electrically coupled to the Hall effect sensor.

10. The method of claim 9, comprising:

sensing a magnitude of the magnetic field using the Hall effect sensor;

comparing the sensed magnitude of the magnetic field to at least one of a specified first threshold or a specified second threshold; and selecting, in response to the comparing, the operating mode of the implantable medical device from a list including at least one of:

(1) a first operating mode when the magnitude of the magnetic field is below the specified first threshold;

(2) a second operating mode when the magnitude of the magnetic field exceeds or equals the specified first threshold over a specified first duration; or (3) a third operating mode when the magnitude of the magnetic field further exceeds or equals the specified second threshold over a specified second duration.

11. The method of claim 10, wherein the selecting the first operating mode includes selecting an ambulatory operating mode;

wherein the selecting the second operating mode includes selecting a battery status test mode and includes providing an indication to a user corresponding to a battery status; and wherein the selecting the third operating mode includes selecting a magnetic resonance imaging (MRI) safe mode.

12. The method of claim 9, comprising controlling one or more excitation parameters associated with the exciting the Hall effect sensor, the one or more excitation parameters including at least one of:

(1) an excitation amplitude;
(2) an excitation pulse width;
(3) a timing between one or more excitation pulses; or
(4) an excitation contact for delivery of the excitation current.

13. The method of claim 9, wherein the Hall effect sensor is rotationally symmetric about an axis.

14. The method of claim 9, wherein the integrated circuit includes a heterostructure configured to increase a Hall mobility associated with the Hall effect sensor.

15. The method of claim 9, wherein the analog-to-digital converter is included in the commonly shared semiconductor integrated circuit.

16. A processor-readable medium including instructions that, when performed by the processor, cause an implantable medical device to:

excite a Hall effect sensor using a polling circuit configured to provide an excitation current to the Hall effect sensor, the polling circuit and the Hall effect sensor included in a commonly-shared semiconductor integrated circuit comprising a portion of the implantable medical device;

sense a magnetic field using a Hall effect sensor, including monitoring at least one of a current or a voltage provided by the Hall effect sensor in response to the sensed magnetic field; and select an operating mode of the implantable medical device using at least one of the current or the voltage; and wherein the monitoring at least one of the current or the voltage includes using an analog-to-digital converter electrically coupled to the Hall effect sensor.

17. The processor-readable medium of claim 16, wherein the instructions include instructions that, when performed by the processor, cause an implantable medical device to:

sense a magnitude of the magnetic field using the Hall effect sensor;

compare the sensed magnitude of the magnetic field to at least one of a specified first threshold or a specified second threshold; and select, in response to the comparing, the operating mode of the implantable medical device from a list including at least one of:

(1) a first operating mode when the magnitude of the magnetic field is below the specified first threshold;

(2) a second operating mode when the magnitude of the magnetic field exceeds or equals the specified first threshold over a specified first duration; or (3) a third operating mode when the magnitude of the magnetic field further exceeds or equals the specified second threshold over a specified second duration.

18. The processor-readable medium of claim 17, wherein the first operating mode includes instructions to select an ambulatory operating mode;

wherein the second operating mode includes a battery status test mode and includes instructions to provide an indication to a user corresponding to a battery status; and wherein the third operating mode includes instructions to select a magnetic resonance imaging (MRI) safe mode.

19. The processor-readable medium of claim of claim 18, comprising instructions that, when performed by the processor, cause the implantable medical device to control one or more excitation parameters associated with the exciting the Hall effect sensor, the one or more excitation parameters including at least one of:

(1) an excitation amplitude;

(2) an excitation pulse width;

(3) a timing between one or more excitation pulses; or (4) an excitation contact for delivery of the excitation current.

* * * * *